United States Patent [19]

Kellermeyer et al.

[11] 4,106,507
[45] Aug. 15, 1978

[54] BLOCKAGE PREVENTION DEVICE FOR BODY FLUID COLLECTION SYSTEMS

[76] Inventors: Janet R. Kellermeyer, 525 Prospect Ave., River Vale, N.J. 07675; Jay M. Alexander, 114 DeGroff Pl., Park Ridge, N.J. 07656

[21] Appl. No.: 718,780

[22] Filed: Aug. 30, 1976

[51] Int. Cl.² .............................................. A61F 5/44
[52] U.S. Cl. ........................... 128/295; 128/DIG. 24
[58] Field of Search ............... 128/272, 273, 274, 275, 128/283, 295, DIG. 24, 214 C

[56] References Cited

U.S. PATENT DOCUMENTS

| 2,700,165 | 1/1955 | Talisman | 128/DIG. 24 |
| 3,881,486 | 5/1975 | Fenton | 128/283 |

*Primary Examiner*—Kyle L. Howell
*Attorney, Agent, or Firm*—Robert A. Maikis

[57] ABSTRACT

A blockage prevention device is provided for ileal conduit urine collection systems of the type having a flexible bag which is coupled to the ileal conduit stoma of a patient to receive urine therefrom. The bag has an outlet located in the neck portion thereof for draining the collected urine to a storage receptacle. The prevention device comprises an elongated member having a fluid-conducting passageway extending therethrough and a plurality of helically-disposed apertures extending through the walls of the member. The member is disposed in the interior of the bag and serves to connect that portion of the interior of the bag lying outside of the neck portion with the bag outlet, so that urine collected in the bag because of a blockage in the neck portion will drain through the member to the bag outlet. The end of the member which is disposed in the bag outlet is provided with a fitting having a collar portion which abuts the bag outlet to limit insertion of the member into the bag.

1 Claim, 5 Drawing Figures

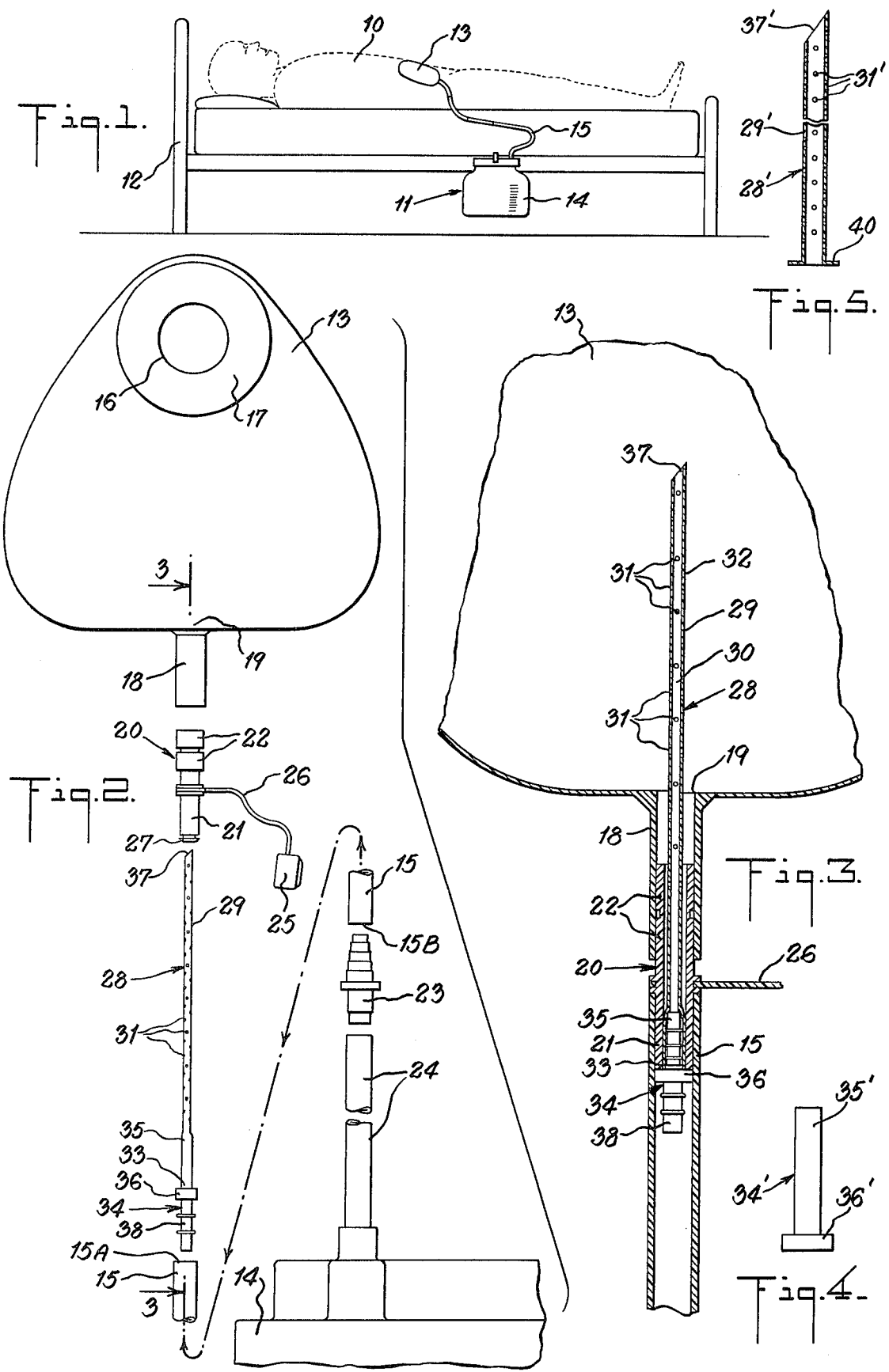

BLOCKAGE PREVENTION DEVICE FOR BODY FLUID COLLECTION SYSTEMS

BACKGROUND OF THE INVENTION

1. Field of the Invention

This invention relates to medical patient care equipment and more particularly to a blockage prevention device for body fluid collection systems of the type having a flexible collection bag which is mounted on the body of a patient to receive body fluids therefrom.

2. Description of the Prior Art

A problem which is frequently encountered in medical practice is the drainage and collection of fluids which accumulate in various cavities of the human body. In the urinary system, catheters are frequently inserted in the urethra to drain the urine which accumulates in the bladder when the patient is incontinent or the urethral canal function is impaired. When the functioning of the bladder itself is impaired, however, or where the drainage must be carried out over a prolonged period of time, an ileal conduit operation may be performed on the patient. In this operation, the ileum, which is the last division of the small intestine extending between the jejunum and the large intestine, is sectioned to form an ileal conduit which is brought out through the abdominal wall of the patient, so that the patient's urine is vented from the body through the ileal conduit instead of passing through the bladder and urethral canal. The patient is provided with a collection bag which is mounted on the abdomen of the patient at the mouth or stoma of the ileal conduit, so that the urine excreted by the patient flows directly into the bag. The collection bags are generally fabricated of a flexible material, such as rubber or a plastic, for example, and are provided with a bag outlet in the neck or bottom portion of the bag through which the collected urine is drained. When the patient is ambulatory, the outlet in the neck portion of the bag is provided with a cap so that the patient may empty the collected urine at suitable intervals of time.

Since the patient has no control over the flow of urine from the ileal conduit, it is customary for the patient to connect the outlet of the bag to a larger capacity, storage receptacle by means of a connection tube when retiring for the night, so that the bag will not fill up when the patient is not awake to empty it. The same collection system is also utilized when the patient is not ambulatory or is physically or mentally unable to empty the ileal conduit collection bag at required time intervals. When the collection bag is coupled by the connection tube to the storage receptacle, however, it frequently happens that the drainage of urine through the outlet of the collection bag is blocked because the flexible bag becomes twisted or folded over upon itself at the neck portion and prevents the fluid in the bag from flowing out through the bag outlet. Since this blockage may occur at night when the patient is asleep or may occur with a patient who is physically or mentally unable to straighten the bag to eliminate the blockage, it becomes important that means be devised to prevent blockages of this type from interfering with the operation of the collection system. A suitable blockage prevention device to solve this problem should be usable with the various types of ileal conduit collection bags which are in use at the present time without the necessity of altering the structure of the bags. Furthermore, the device itself should be easily manufactured and maintained.

SUMMARY OF THE INVENTION

It is an object of this invention to provide a blockage prevention device for body fluid collection systems of the flexible bag type which may be employed with the various types of collection bags in use at the present time without modifying the structure of the bags.

It is a further object of this invention to provide a blockage prevention device for body fluid collection systems of the flexible bag type which is reliable and safe in operation for all types of patients.

It is a still further object of this invention to provide a blockage prevention device for body fluid collection systems of the flexible bag type which is simple in construction and operation and is easily manufactured and maintained.

It is an additional object of this invention to provide a blockage prevention device which is particularly suitable for use with ileal conduit urine collection systems of the flexible bag type.

Briefly, the blockage prevention device of the invention comprises an elongated member disposed in the interior of the flexible, body fluid collection bag and having one end thereof extending through the bag outlet to the exterior of the bag and the other end thereof extending through the neck portion of the bag to that portion of the interior of the bag outside of the neck portion. The elongated member has insertion limiting means at said one end of the member for limiting insertion of the member into the bag, walls defining a passageway extending through the member along the length thereof, and a plurality of apertures extending through the walls at spaced points along the length of the member to connect the passageway to the exterior of the member. Accordingly, fluids collecting in the bag because of a blockage in the neck portion thereof are drained through the apertures and passageway of the member to the bag outlet. The insertion limiting means may comprise a section of the member having a cross-sectional area greater than the cross-sectional area of the bag outlet, so that the member section abuts the bag outlet to limit insertional movement of the member into the bag. Alternatively, the insertion limiting means may comprise an integral connection between said one end of the member and the bag outlet, so that movements of the member both into and out of the bag are prevented.

The nature of the invention and other objects and additional advantages thereof will be more readily understood by those skilled in the art after consideration of the following detailed description taken in conjunction with the accompanying drawings.

BRIEF DESCRIPTION OF THE DRAWINGS

In the drawings:

FIG. 1 is a side elevational view showing a bed patient filled with an ileal conduit urine collection system of the flexible type;

FIG. 2 is an exploded plan view of the ileal conduit urine collection system of FIG. 1 with a blockage prevention device constructed in accordance with the teachings of the present invention;

FIG. 3 is a full sectional view taken along the line 3—3 of FIG. 2 with the parts of the collection system in assembled position;

FIG. 4 is a plan view of an alternative form of the insertion limiting means for the blockage prevention device shown in FIGS. 2 and 3 of the drawings; and FIG. 5 is a full sectional view of another alternative form of the insertion limiting means for the blockage prevention device of the invention.

DESCRIPTION OF THE PREFERRED EMBODIMENT OF THE INVENTION

Referring now to FIG. 1 of the drawings, a patient 10 fitted with an ileal conduit urine collection system indicated generally as 11 is shown in a bed 12. The urine collection system 11 comprises a flexible collection bag 13 which is mounted on the abdomen of the patient, a storage receptacle 14 which is mounted on the bed 12 and a connection tube 15 which interconnects the collection bag 13 and the storage receptacle 14. As seen in FIG. 2 of the drawings, the collection bag 13 has an inlet opening 16 which is surrounded by a flat annular collar 17 and an outlet opening 18 which is disposed in the neck portion 19 of the bag. The outlet opening 18 is provided with an outlet fitting or adapter indicated generally as 20. The fitting 20 has a hollow cylindrical body 21 one end of which is inserted in one end 15A of the connection tube 15 to form a fluid-tight connection therewith. Two shoulders 22 having a diameter larger than the diameter of the body 21 of the fitting are formed on the other end of the body 21 and are inserted in the outlet opening 18 of the collection bag to form a fluid-tight connection therewith, so that the outlet opening 18 and the outlet fitting 20 cooperate to form the bag outlet through which the urine collected in the bag is drained. The other end 15B of the connection tube 15 is connected to the storage receptacle 14 by means of a conventional tubing connector 23 and the input tubing 24 of the storage receptacle. The storage receptacle 14 functions to provide a suitably large storage capacity for the urine excreted by the patient through the collection bag 13 and the tube 15 and may comprise any one of a number of commercially-available types, such as the flat bag type illustrated, for example.

The ileal conduit bag 13 is a commercially-available item which is usually fabricated of a flexible material, such as rubber or a plastic, for example. When the ileal conduit operation is completed and the stoma of the ileal conduit is brought out through the abdominal wall of the patient, the annular collar 17 of the collection bag 13 is mounted on the patient's abdomen around the stoma by means such as an adhesive, for example, so that a fluid-tight connection is made between the collection bag and the patient. The urine excreted by the patient through the ileal conduit stoma then passes through the inlet opening 16 of the bag and is collected in the neck portion 19 of the bag. When the patient is ambulatory, the outlet adaptor 20 is provided with a cap 25 which is secured to the adapter by a flexible strip or tether 26 and which is employed to cap or seal the end 27 of the bag outlet so that urine excreted by the patient collects in the bag 13. The patient then empties the collection bag as often as may be necessary into a toilet or other disposal means.

When the patient is permanently bedridden or when an ambulatory patient retires to bed for the night, the cap 25 is removed from the outlet fitting 20 and the storage receptacle 14 is connected to the bag outlet by means of the flexible tube 15, so that urine collecting in the bag 13 is continuously drained from the bag into the storage receptacle. When this collection system is utilized, it frequently happens that the flexible bag 13 becomes twisted or folded at the neck portion 19 of the bag by the patient's movements. The twisting or folding of the bag creates a blockage in the neck portion 19 which prevents the urine excreted by the patient into the bag from draining through the bag outlet and connection tube 15 into the storage receptacle 14. Since the patient may be asleep, the blockage may not be discovered until the collection bag 13 becomes dangerously full of urine. A similar situation could occur when the ileal conduit patient suffers from a mental or physical disability which would prevent him from personally eliminating the blockage in the collection bag.

The blockage prevention device of the invention is shown in FIGS. 2 and 3 of the drawings as comprising an elongated member, indicated generally as 28, which is inserted into the interior of the bag 13 through the bag outlet. The member 28 may comprise a length of cylindrical tubing 29 having a fluid-conducting passageway 30 extending therethrough along the length of the tubing. The tubing 29 is provided with a plurality of apertures 31 extending through the walls 32 of the tubing at spaced points along the length thereof to connect the passageway 30 to the exterior of the tubing. One end 33 of the elongated member 28 is provided with insertion limiting means, indicated generally as 34, to limit insertion of the member into the collection bag, so that the end 33 of the member extends through the bag outlet to the exterior of the bag. The insertion limiting means 34 is shown in FIGS. 2 and 3 of the drawings as comprising a hollow cylindrical fitting 35 which is inserted in an end of the cylindrical tubing 29 with a fluid-tight fit. The fitting 35 has a collar or shoulder portion 36 of increased diameter, so that the cross-sectional area of the collar 36 is greater than the cross-sectional area of the bag outlet fitting 20. Accordingly, when the member 28 is inserted into the collection bag through the bag outlet, the collar 36 abuts the end 27 of the bag outlet and limits the insertion of the member, so that one end of the member always extends through the bag outlet to the exterior of the bag. The length of the elongated member 28 is such that the other end 37 of the member extends through the neck portion 19 of the collection bag to that portion of the interior of the bag which is outside of the neck portion. Accordingly, the apertures 31 and passageway 30 of the member serve to connect the exterior of the bag to that portion of the interior of the bag which is outside of the neck portion.

When the flexible bag 13 becomes twisted or folded so that the neck portion 19 of the bag becomes blocked and urine accumulates in the bag in that portion of the interior of the bag outside of the neck portion, the accumulated urine will flow through the apertures 31 in the walls 32 of the member 28 and thence through the passageway 30 into the end 15A of the tube 15 at the bag outlet. By virtue of this arrangement, no matter which way the bag 13 is twisted or folded, the elongated member 28 still provides a communicating passageway between the accumulated urine in the bag and the bag outlet opening 27. Since the apertures 31 are disposed at points along the length of the member, fluids collecting in the neck portion 19, the outlet 18 and the outlet fitting 20 will also be drained.

The elongated member 28 comprises the tubing 29 and the fitting 34 which functions as the insertion limiting means. These parts should be fabricated of a material which will not chemically react with urine. The material for the tubing 29 should have sufficient rigidity to permit the member 28 to be inserted through the bag outlet to the proper depth, so that the end 37 of the member always lies outside of the neck portion of the bag. At the same time, the material for the tubing 29 should be sufficiently flexible to prevent the end 37 of the member from puncturing the thin walls of the collection bag during insertion of the member or use of the system. For example, the tubing 29 could be made of polyethylene which is a flexible thermoplastic which is resistant to chemicals and moisture. The fitting 34 of the member, which need not be flexible, may be fabricated of any material which will not react with urine or water. The apertures 31 which are formed in the walls 32 of the member are preferably helically disposed along the length of the member, so that the apertures will be disposed at different locations around the circumference of the member. This will avoid the possibility that all of the apertures could be sealed or closed by the interior walls of the bag 13 pressing against the member. No matter what position the member assumes in the bag, some of the apertures will communicate with the interior of the bag to drain the accumulated fluid.

The blockage prevention device of the invention is shown in FIGS. 2 and 3 of the drawings as being applied to a flexible collection bag 13 having an outlet adapter 20 which has the cap 25 for daytime use by ambulatory patients. It will be understood, however, that the outlet adapter 20 could be replaced by any one of a number of commercially-available "nighttime" adapters which do not have the cap or other sealing means and which are only provided with a male cylindrical fitting for insertion into the connection tube 15 leading to storage receptacle 14. Since the distance to which the blockage prevention member 28 of the invention is inserted into the collection bag is limited by the collar 36 of the member, the diameter of the tubing 29 of the member may be made sufficiently small to permit insertion of the member into virtually all of the bag outlet adapters on the market today, so that the blockage prevention device is usable with all of the principal types of ileal conduit collection bags presently available. The outside diameter of the portion of the adapter which is inserted into the connection tube 15 is usually standardized in the various types of commercially-available adapters so that standard connection tubes may be used. Accordingly, the diameter of the collar 36 on the device of the invention may be made approximately the same as the outside diameter of the cylindrical body 21 of the outlet adapter 20, so that the member 28 will be prevented from sliding into or out of the bag by the frictional engagement of the collar 36 with the flexible connection tube 15.

The insertion limiting means 34 which is shown in FIGS. 2 and 3 of the drawings may conveniently comprise a commercially-available tubing connector for connecting tubing of different sizes and is accordingly illustrated as including a cylindrical portion 38 having a diameter somewhat larger than the portion 35 which is inserted into the tubing 29. Although the portion 38 may be useful as a "handle" to permit easy manual insertion of the blockage prevention device into the bag 13, it may be omitted, if desired. Accordingly, the insertion limiting means 34 may comprise only the hollow cylindrical fitting 35' and the collar or shoulder portion 36' thereof as shown in FIG. 4 of the drawings where the reference numerals with a prime notation are employed to designate the correspondingly numbered parts of the embodiment of FIGS. 2 and 3 of the drawings. It will also be understood that the blockage prevention device 28 could comprise a single integral unit instead of the separate length of tubing 29 and the fitting 34 which have been described. Since the collar 36 of the fitting 34 merely functions as a section of the member 28 having a cross-sectional area larger than the cross-sectional area of the bag outlet, it is apparent that the tubing 29 and the collar 36 could be fabricated as a single integral unit. An arrangement of this type is shown in FIG. 5 of the drawings wherein reference characters with a prime notation are employed to designate parts which are the same as or similar to corresponding parts in the embodiment of the invention shown in FIGS. 2 and 3 of the drawings. As seen in FIG. 5, the member 28' could comprise a length of tubing 29' having an annular section 40 of increased diameter formed at one end thereof which would abut the end 27 of the bag outlet adapter 20 to limit insertion of the member into the bag. The collar 40 is an integral part of the tubing 29' in this embodiment of the invention. Finally, it is believed obvious that the insertion limiting means need not comprise a collar or any tubing section of larger diameter since the end of the tubing section 29 of the member 28 could be secured or affixed to the end 27 of the bag outlet adapter to limit insertion of the member into the bag. In this case, the insertion limiting means would be an integral connection between the end of the member and the bag outlet, so that movements of the blockage prevention member both into and out of the bag are prevented. The integral connection could be made by cementing or fusing the end of the tubing 29 to the bag outlet adapter or fabricating these parts as a single unit.

It is believed apparent that many changes could be made in the construction and described uses of the foregoing blockage prevention device and many seemingly different embodiments of the invention could be constructed without departing from the scope thereof. Although the invention has been described as being used with an ileal conduit urine collection system, it may obviously be employed with other body fluid collection systems of the flexible bag type. For example, the flexible collection bags described herein may be used to drain various body cavities or open wounds and the like and the blockage prevention device of the invention could be utilized in such systems. Accordingly, it is intended that all matter contained in the above description or shown in the accompanying drawings shall be interpreted as illustrative and not in a limiting sense.

What is claimed is:

1. In a body fluid collection system, the combination comprising
 a flexible collection bag having
  a bag inlet adjacent one end thereof adapted to be coupled to the stoma of a patient to receive body fluids therefrom,
  a neck portion at the other end thereof, and
  a bag outlet in said neck portion for draining fluids from the bag, said bag outlet comprising a hollow cylindrical adapter;
 a connection tube having said adapter inserted into one end thereof, the other end of said tube being adapted to be coupled to a body fluid storage receptacle; and
 an elongated blockage prevention member comprising a length of cylindrical tubing removably disposed in the interior of said bag having one end thereof extending through said bag outlet to the exterior of said bag and the other end thereof extending through said neck portion of the bag to that portion of the interior of the bag outside of the neck portion, said cylindrical tubing having walls defining a passageway extending through said tubing along the length thereof and a plurality of apertures extending through said walls at spaced points along the length of the tubing to connect said passageway to the exterior of said tubing, and a hollow cylindrical fitting having one end thereof inserted in said one end of said cylindrical tubing and the other end thereof having a collar formed thereon, said collar having a cross-sectional area greater than the cross-sectional area of said bag outlet, so that said collar abuts the bag outlet exteriorly of the bag to limit insertional movement of said member into the bag, said collar having a diameter substantially the same as the diameter of said adapter, so that said collar is held in place against the adapter by said connection tube to prevent withdrawal of said member from said bag, whereby body fluids collecting in said bag because of a blockage in the neck portion thereof are drained through said apertures and said passageway of the blockage prevention member to said bag outlet.

* * * * *